(12) United States Patent
Ghosh et al.

(10) Patent No.: US 7,833,161 B2
(45) Date of Patent: Nov. 16, 2010

(54) BONE DENSITOMETER AND A METHOD THEREOF

(75) Inventors: Rajdeep Ghosh, Karnataka (IN); Somashekar Umadi, Karnataka (IN); Raj Agarwal, Karnataka (IN); Nagarajan Ravindran, Karnataka (IN); Mosale Nageshrao Sowmya, Karnataka (IN)

(73) Assignee: Larsen & Toubro Limited (IN)

( * ) Notice: Subject to any disclaimer, the term of this patent is extended or adjusted under 35 U.S.C. 154(b) by 705 days.

(21) Appl. No.: 11/503,017

(22) Filed: Aug. 11, 2006

(65) Prior Publication Data
US 2007/0078341 A1    Apr. 5, 2007

(30) Foreign Application Priority Data
Oct. 3, 2005 (IN) .................. 1401/CHE/2005

(51) Int. Cl.
*A61B 8/00* (2006.01)
(52) U.S. Cl. .................. 600/449; 600/442; 600/437; 600/438
(58) Field of Classification Search .................. 600/437, 600/438, 442, 449
See application file for complete search history.

(56) References Cited

U.S. PATENT DOCUMENTS

| | | | |
|---|---|---|---|
| 5,603,325 A * | 2/1997 | Mazess et al. | 600/442 |
| 6,585,649 B1 * | 7/2003 | Mendlein et al. | 600/438 |
| 2002/0007119 A1 * | 1/2002 | Pelissier | 600/443 |
| 2002/0103435 A1 * | 8/2002 | Mault | 600/439 |
| 2005/0215908 A1 * | 9/2005 | Chew et al. | 600/459 |
| 2006/0122475 A1 * | 6/2006 | Balberg et al. | 600/323 |

* cited by examiner

*Primary Examiner*—Long V Le
*Assistant Examiner*—Nigel Fontenot
(74) *Attorney, Agent, or Firm*—Donald R. Boys; Central Coast Patent Agency, Inc.

(57) ABSTRACT

The present invention provides a system for improving the accuracy of the measurement of the osteoporosis condition of the human body parts especially bones using more than three parameters, viz., the broadband ultrasonic attenuation (BUA) quantity, the velocity of ultrasound (SOS) in the bone, the broadband ultrasonic back scattering (BUB) intensity, and the Width of received maximum (WORM) values are calculated from received ultrasound signals.

The accuracy of each measured diagnostic parameter is improved by measuring the tissue thickness and the squish amount in the coupling pad instead of assuming constant thickness for the tissue. The several operating modes of the device are controlled and the frequency and the timing of the emitted ultrasounds signals are adjusted by using a field programmable gate array. The error generated in the measurement of the bone mineral density due to the variation in the anatomy and the size of the foot, is removed by using a removable footpad. The present invention provides a mechanism to replace the gel pads easily. The generation of cross infection is prevented by using the disposable and replaceable coupling pads.

19 Claims, 8 Drawing Sheets

BONE DENSITOMETER AND A METHOD THEREOF

FIELD OF THE INVENTION

This invention relates generally to methods and devices for assessing bone conditions, and more particularly related to a method and a device for assessing bone properties such as, for example, bone mineral density and bone micro-architecture for diagnosis of bone conditions like osteoporosis, etc using ultrasound technique.

BACKGROUND OF THE INVENTION

Osteoporosis is a phenomenon resulting in the weakening of the bones due to the reduction in bone mineral density and changes in the micro architecture of bone due to the depletion of minerals like calcium and bone protein. The evaluation of osteoporosis or the loss of bone minerals and the treatment or prevention of the osteoporosis is performed by usually measuring the bone density.

Some of the devices used for measuring the bone density include X-ray device, gamma ray detector device and ultrasound device, etc. In general, a system used for conducting the bone analysis using the ultrasound, comprises a pair of transducers between which the part of the human body to be analyzed is positioned. One of the two transducers emits ultrasonic waves, while another transducer receives the ultrasonic waves from the human body part under analysis. The elasticity and the density of the bone are measured using the calculated velocity of the ultrasonic signal (SOS) through the bone of a patient. A clear picture of bone density and the micro architecture of cancellous bone are acquired by calculating the broadband ultrasonic attenuations (BUA) in bones. The attenuation of the ultrasound signals with a frequency of 200 KHz-600 KHz, is measured.

A doctoral thesis by Langton entitled "The measurement of broadband ultrasound attenuation in cancerous bone" dated July 1984, explains the measurement of the velocity of sound and broadband ultrasonic attenuation (BUA) through the Os calcis of the heel.

Also, U.S. Pat. No. 5,054,490 discloses a technique to measure the BUA and SOS in bones after immersing the heel of patient in water.

In some conventional bone assessment techniques such as, for example, a QUS technique, for measuring the physical properties of the bone, there are several sources of error and factors that reduce the accuracy and the precision of the measurement result. For example, the assumption of a soft tissue of fixed thickness around the heel during the estimation of ultrasound velocity generates an error in SOS measurement. The precision and the accuracy of the measurement are varied with respect to the variation in thickness of the soft tissue. The thickness of the soft tissue is varied due to the loss or gain of weight or due to the development of the ankle edema. Moreover, the BUA measurement result acquired from the above-mentioned methods is varied with respect to the variation in bone width. Since both the BUA and SOS values are used independently to calculate the bone mineral density (BMD), the accuracy of the measurement of the parameters is not sufficiently high.

An error is also generated in speed of sound (SOS) measurement during the usage of dry coupling pads due to the variation in the quantity of squish in the coupling pad on contact with the heel of subject depending on the shape of the heel of the patient. So the squish in the coupling pads is to be measured accurately instead of assuming a fixed amount of squish compensation.

Moreover, an error in the measurement of SOS Parameters is generated due to the variation in the timing signals like activating time, switching time of ultrasound transducers and time of detection of received ultrasound signal at receiver above a specified threshold due to the limitation of hardware and processing speed. Even a small variation caused due to abovementioned factors induces unacceptable variation in various diagnostic parameters. Hence there is a need to accurately control the various timing signals.

All the ultrasound based measurement devices using dry coupling pads (gel pads) do not provide sufficient safety from cross infection as the same set of coupling pads is used for several patients. There is also a need for a method to remove the gel pads easily. Hence there is a need to improve the accuracy of bone density measurement and to prevent cross contamination among several patients.

OBJECTS OF THE INVENTION

An object of this invention is to additionally analyze the reflected and scattered ultrasonic signals in addition to the transmitted signals for measuring the bone condition.

An object of the invention is to improve the accuracy and the sensitivity of the measurement of bone characteristics by using a multi variable approach and by utilizing more than three (and ideally four) parameters to assess the bone status completely and to improve the accuracy of diagnosis.

An object of the invention is to improve the accuracy in calculating the velocity of the sound through the heel by calculating the thickness and instead of assuming a fixed thickness for the soft tissue surrounding the calcaneous.

An object of the invention is to improve the accuracy of calculating the velocity of sound through the heel by computing the coupling pad thickness (amount of squish) on both sides of the heel instead of assuming a fixed amount of squish for the coupling pads during SOS measurement process.

An object of the invention is to perform a multi-site measurement, instead of measuring the bone density at heel. The bone status is evaluated using the reflected signal, there by using a signal a transducer to carry out the measurements at several locations.

An object of the invention is to use an advanced programmable logic like field programmable gate array (FPGA) along with digital signal processor (DSP) instead of using conventional analog, digital and micro processor based system to control several timing signals accurately to reduce the error in the measurement of several diagnostic parameters.

An object of the invention is to use the easily replaceable and disposable coupling pads (gel pads) so that the cross infection among several patients is prevented by using easily replaceable and disposable coupling pads. The gel pads are also bacteriostatic.

An object of the invention is to use a footpad that is removed for subjects having foot size above a specified level, to accommodate various foot sizes and to ensure a desired region of interest.

DETAILED DESCRIPTION OF INVENTION

Figure 1:
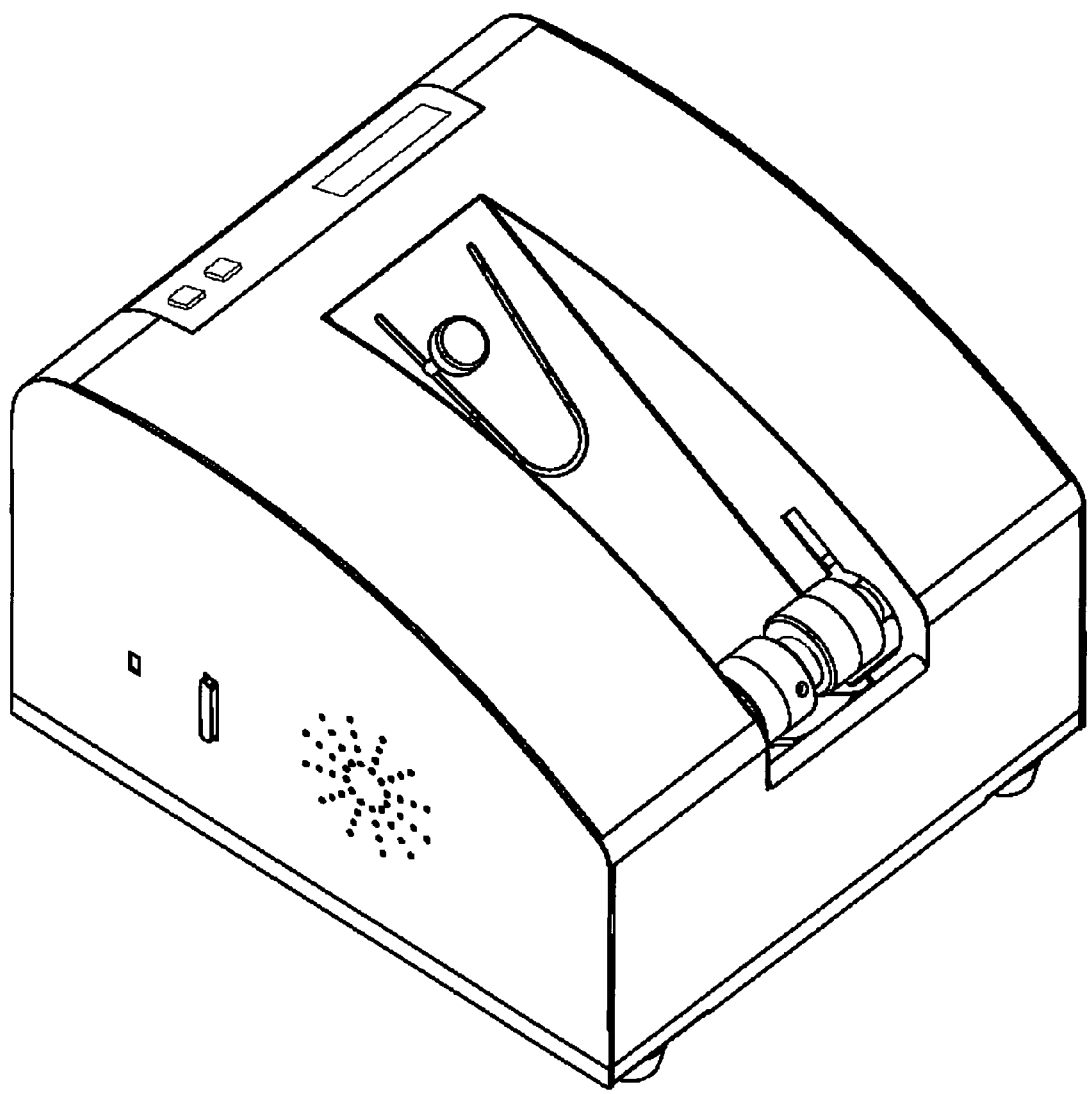
FIG. 1 shows the perspective view of the ultrasound bone analyzer for measuring bone condition according to an embodiment of this invention.

FIG. 1 shows an embodiment of a bone condition assessment device according to this invention. Accordingly, the device has a movable assembly provided at both ends with an ultrasonic transducer so that the transducers at both ends are moved towards or away from each other. The transducer acts as a transmitter or a receiver or a transceiver. The transducers may or may not be in direct contact with the body part such as heel or any other bone under test of a subject or human being. The transducers are removable and may be used as a single entity to measure or analyze the bone condition without requiring another transducer. Thus, it should be noted that the measurement site is not restricted to heel and the measurement may be carried out in any location. A foot receptacle is provided to receive a body part such as heel.

Figure 2:
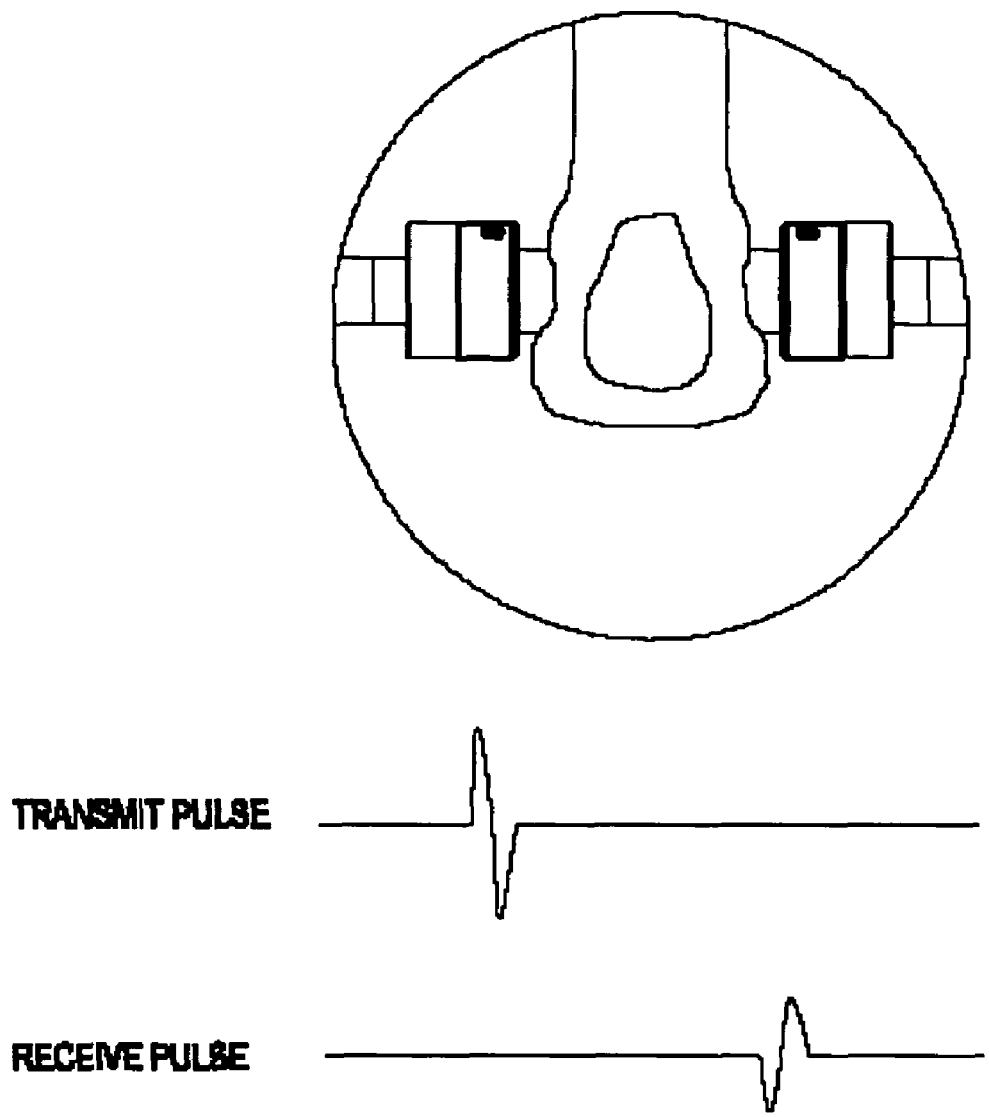
FIG. 2 shows an enlarged arrangement view of transducer in one specific mode in which one transducer transmits ultrasonic signals while the other transducer receives ultrasound signals according to an embodiment of this invention.

FIG. 2 shows an example of an arrangement of transducer wherein another transducer receives the ultrasound emitted by one transducer. The human body part to be analyzed is positioned between the two transducers. The transducers are arranged to accommodate body part of any size. The gap between the transducers is adjusted freely. A signal processing and acquisition circuit receives and processes the ultrasonic signals transmitted and reflected from the heels that are provided between the transducers, to calculate the four parameters, namely the speed of ultrasound (SOS) through the bone in the body part under investigation, the amount of attenuation of ultrasound (BUA) in human body part, the broadband ultrasonic backscattered value (BUB) and the change in shape of the received ultrasound in time domain i.e. width of received maximum(WORM), to calculate the bone density and characteristics.

Figure 3:
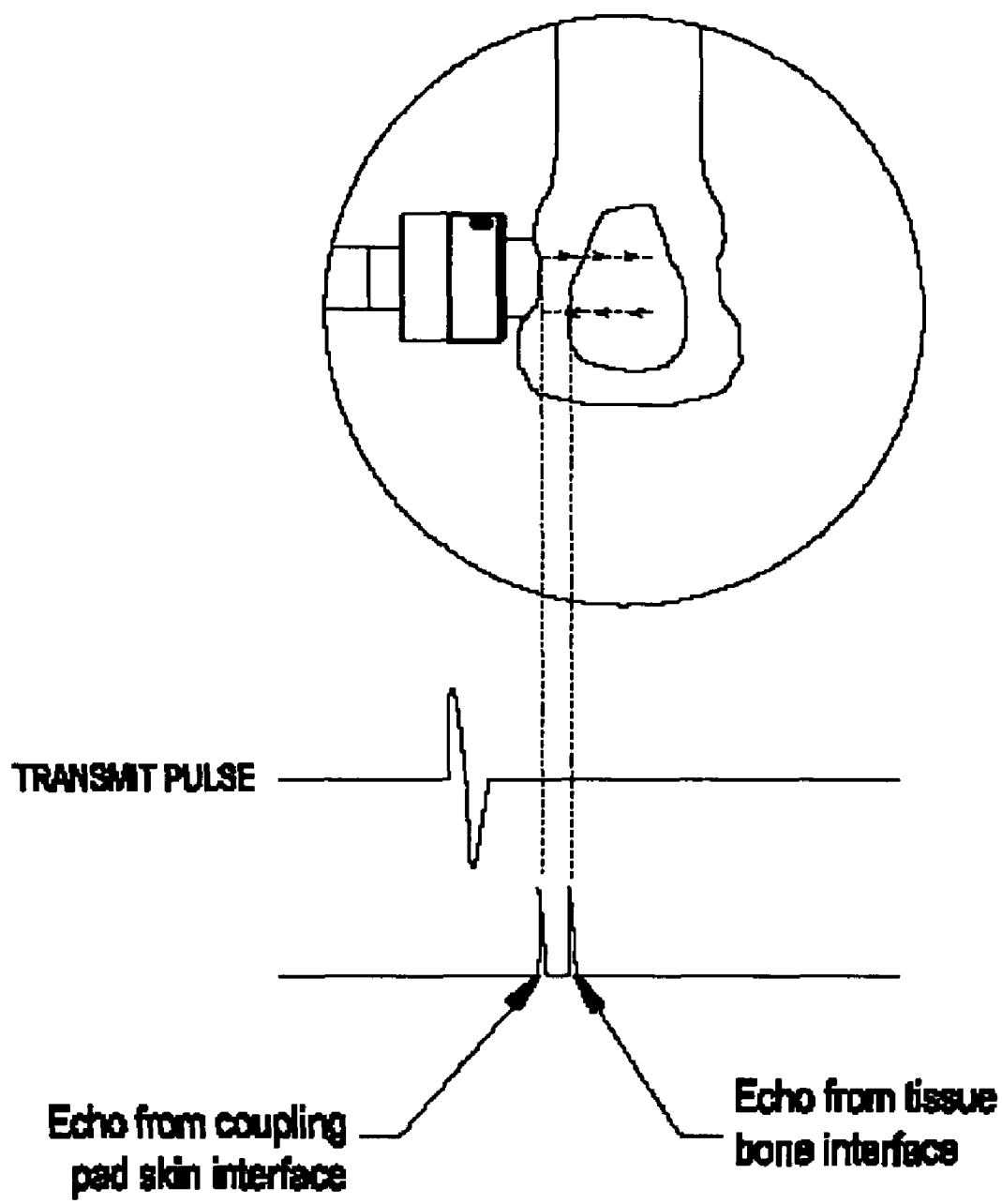
FIG. 3 shows one operating mode of bone densitometer in which one transducer transmits and receives reflected signals for calculating coupling pad and heel tissue thickness according to an embodiment of this invention.

FIG. 3 shows an embodiment wherein a single transducer is used both to transmit and receive ultrasound signals from human body under diagnosis. This arrangement helps to calculate the squish in the coupling pads and to calculate the thickness of soft tissue, which surrounds the heel, instead of assuming a fixed amount of squish and tissue thickness.

Figure 4:
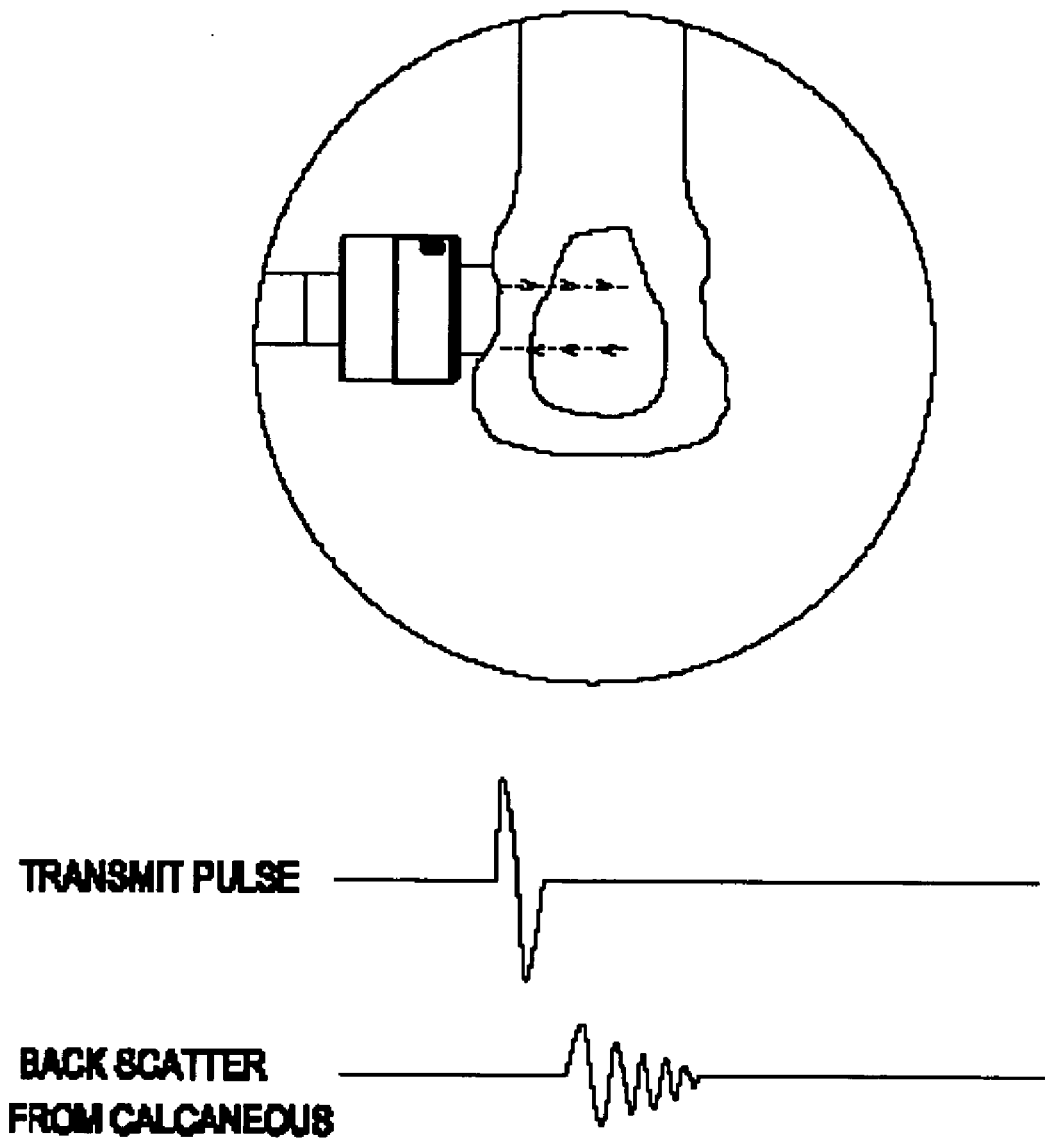
FIG. 4 shows an operating mode of densitometer in which a single transducer transmits and receives reflected signals from bone to analyze bone condition according to an embodiment of this invention.

FIG. 4 shows an embodiment wherein a single transducer is used both to transmit and receive ultrasound signals from the human body under diagnosis to analyze the back scattered and reflected signals for evaluating bone characteristics.

Figure 5:
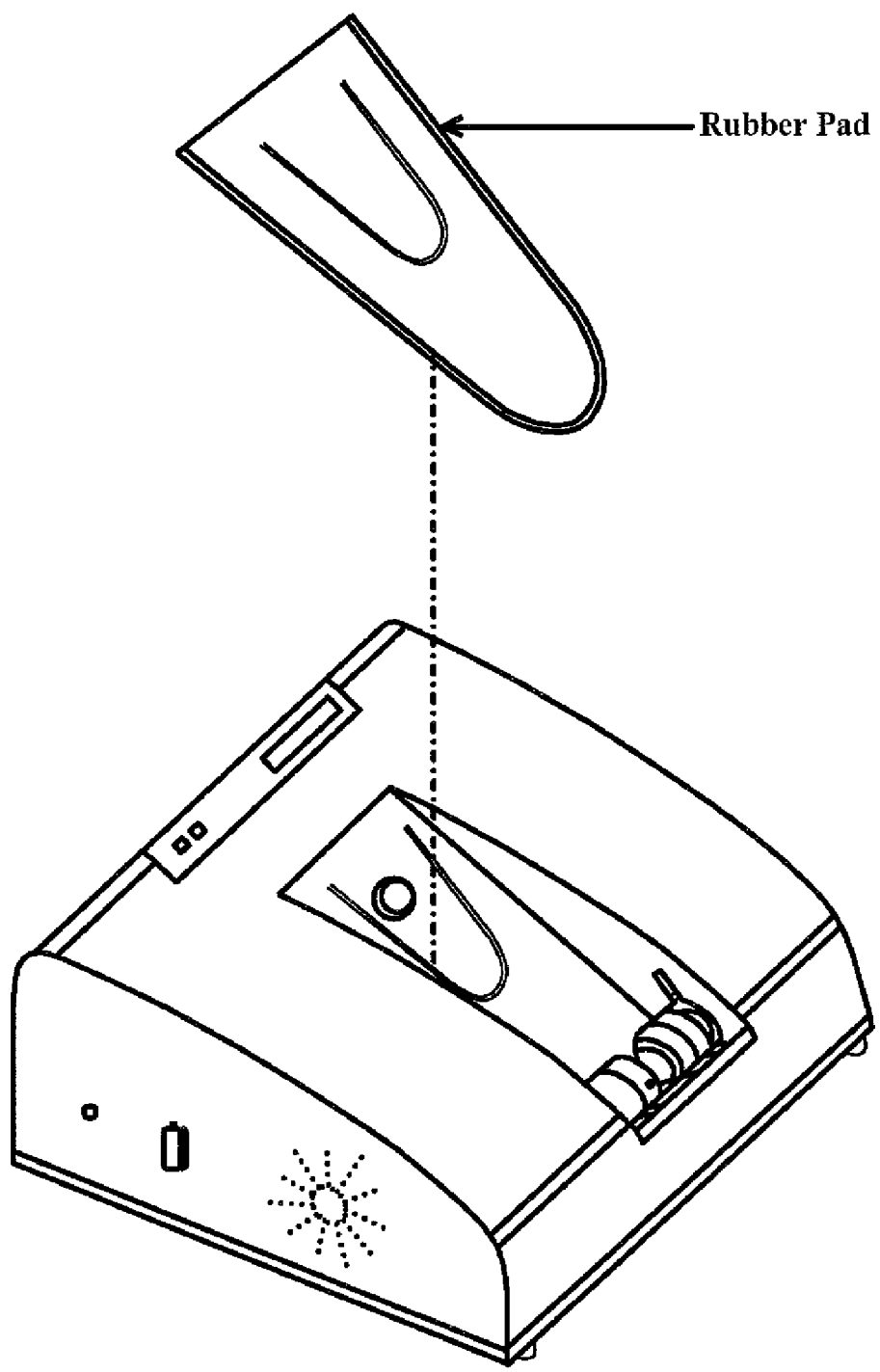
FIG. 5 shows the perspective views of bone analyzer of present invention and removable footpad for acquiring the desired region of interest according to an embodiment of this invention.

FIG. 5 shows an embodiment wherein the removable foot pad enables keeping the desired region of interest of foot with different sizes at the calcaneous.

Figure 6:
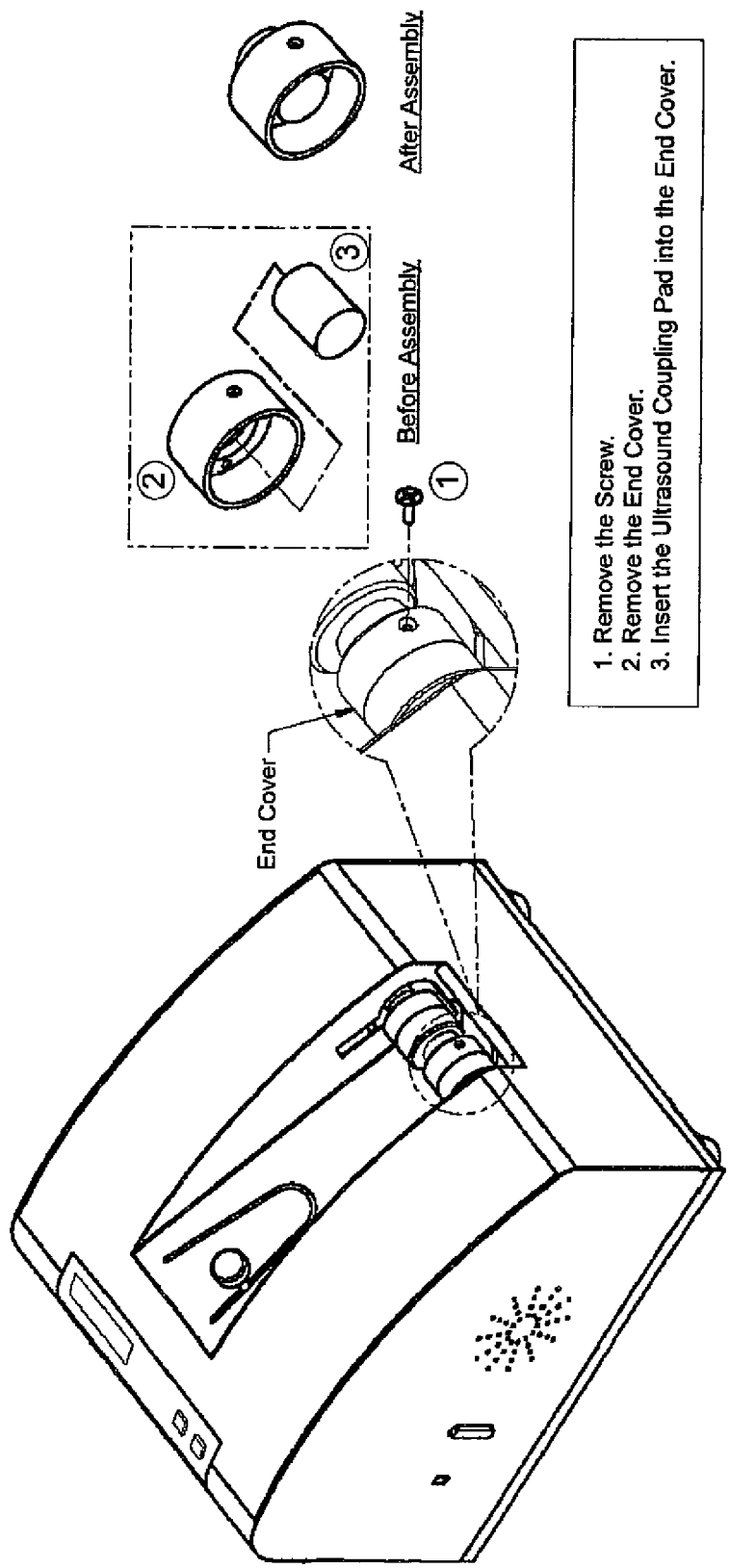
FIG. 6 shows the perspective view of bone analyzer and the enlarged and exploded perspective views of end cover before and after assembly according to an embodiment of this invention

FIG. 6 shows an embodiment wherein easily removable and disposable coupling pads are provided, that is bacteriostatic and damaged between two measurements. An outer case holding the disposable coupling pad is removed easily from the transducer assembly. The outer case is fixed back to the transducer assembly, after replacing the pads.

Figure 7:
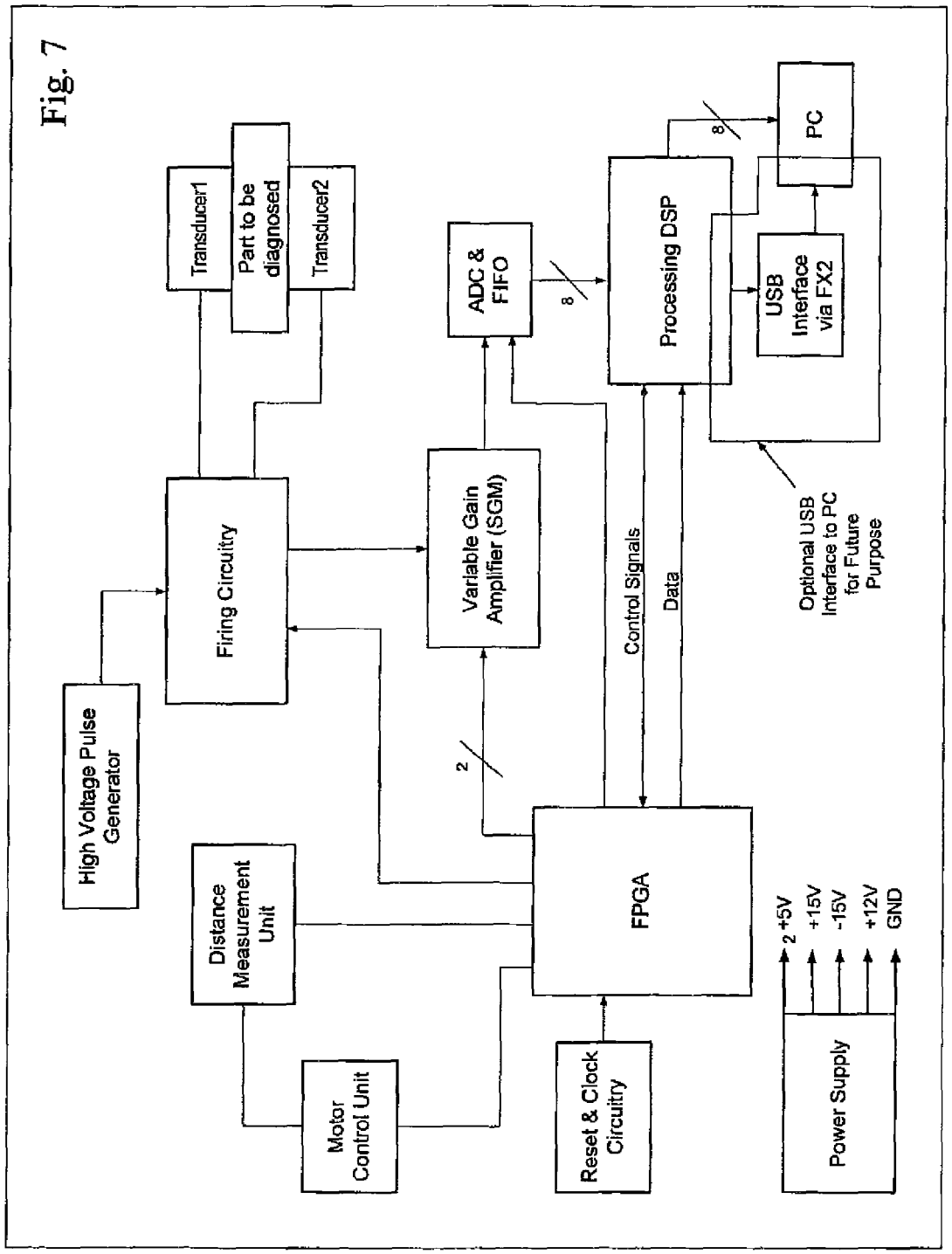
FIG. 7 shows the block diagram of the ultrasound bone analyzer according to an embodiment of this invention.
Figure 8:
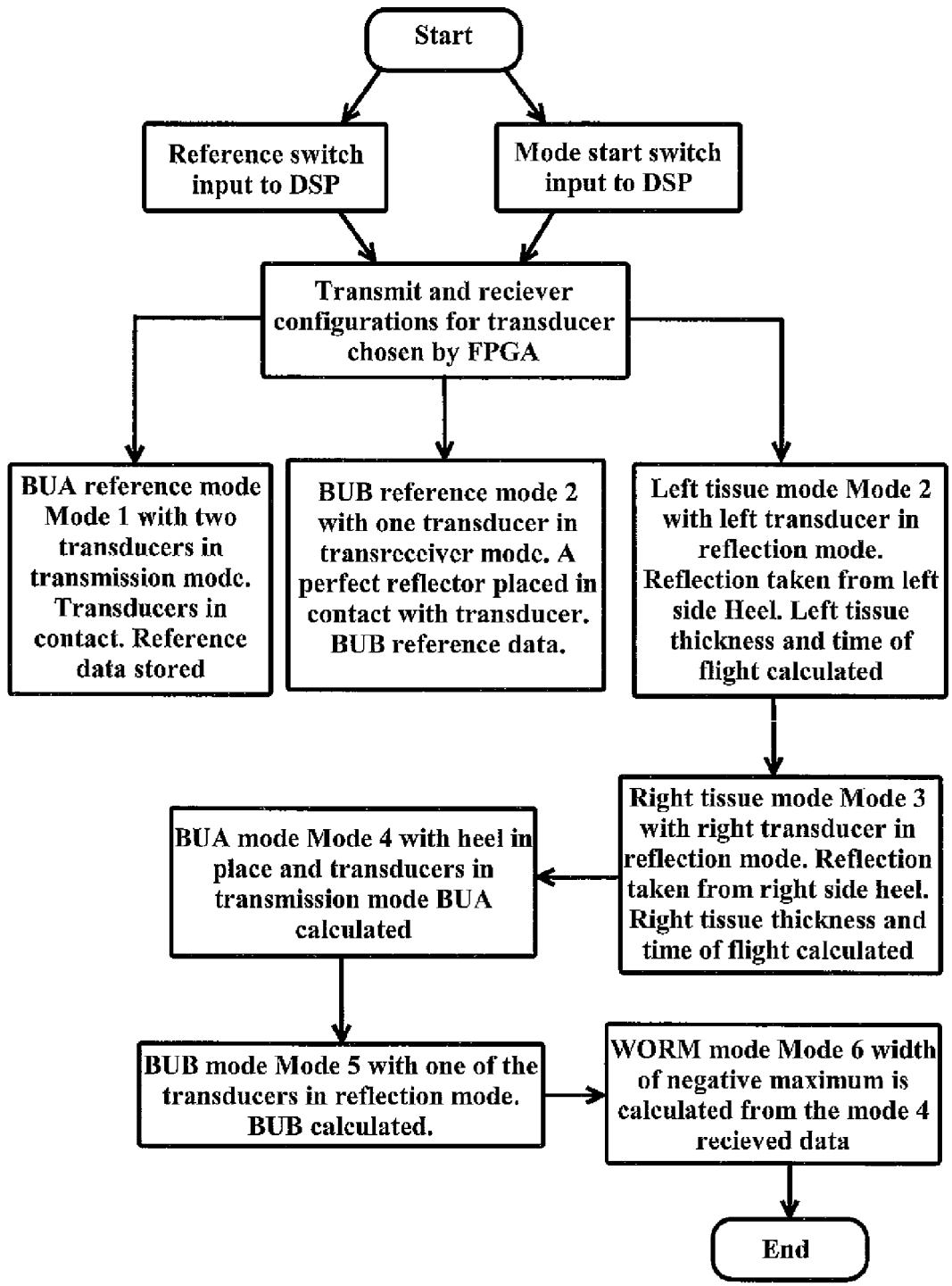
FIG. 8 shows a flow chart explaining the operating method of ultrasound bone analyzer according to an embodiment of this invention.

FIG. 7 shows an example of a block diagram according to this invention wherein transducers (1), (2) are connected to a firing circuit, which triggers an ultrasonic pulse. A field programmable gate array (FPGA) controls the activation timing of firing circuit for acquiring the ultrasound signal of desired band with and for activating the relay switch. The FPGA controls the mode of firing and receiving of the transducer i.e. transmitting mode, receiving mode, or transceiver mode. The FPGA triggers the relay switch (analog switch) to accept the received signal from the transducer (2) operated in transmitting mode or from the transducer (1) operated in transceiver mode, after the input of ultrasonic pulse (high voltage pulse) through the transducer (1). The transducer (2) transmits the received ultrasound signal from the transducer (1) to a variable gain amplifier. The amplified analog signal is converted into a digital signal using an analog to digital (A/D) converter. The generated digital signals are forwarded to a digital signal processor or personal computer that processes the received signals to calculate different parameters to estimate the bone status. The signal processing operation is performed both in time domain and in frequency domain. The frequency domain calculation is used to calculate broadband ultrasonic attenuation (BUA), which is calculated in a transmission mode and broadband ultrasonic scattering in reflection mode. The time domain signal processing is performed to calculate speed of sound (SOS) and width of received maximum (WORM) i.e. the full width of half maximum value of received ultrasonic signal. The FPGA is also connected to a clock circuit and to a distance measurement unit, which acquires the separation between the two transmitters. The acquired data is used in the measurement of speed of ultrasound through the bone and the measurement of squish in the coupling pads and in tissue surrounding the bone. The transmitted and the received ultrasound signals are used to calculate thickness of squish and tissue, and speed of ultrasound by calculating time of arrival of various received and transmitted signals. The calculated information is provided to DSP or PC for calculating the speed of ultrasound through bone, after removing the effect of tissue and the coupling pad on the speed of ultrasound measurement.

In an embodiment, a USB and a parallel port interface is provided between digital signal processor and PC so that the signals are processed in DSP as well as in PC.

FIG. 9 shows a system flow chart that indicates the operation of bone densitometer. The system is operated in multiple modes. In the BUA reference mode, both the transducers are made to contact each other. The signal transmitted with one transducer is received by another transducer. The received signals in reference mode of operation are recorded for BUA reference data for further calculations. A reflector is provided in contact with the same transducer, which transmits and receives the reflected echo. The received data is recorded as BUB reference data for further calculations. In the left tissue mode, the left transducer is operated in a transceiver mode so that the left tissue thickness and coupling pad squish are calculated based on received reflected signal from the left side of the heel and based on the time of arrival of signals from different interfaces. Similarly in the right tissue mode, the right transducer is kept in transceiver mode. The right tissue thickness and the coupling pad squish are calculated based on the reflected signals from the right side of the heel. The speed of sound through the bone is derived based on calculated left and right side tissue thickness levels and calculated squish, after removing the influence of the surrounding tissue and coupling pads.

In an example, in BUA mode, one transducer acts as a transmitter and the other transducer is operated in the receiving mode. The acquired signal in BUA mode is compared with the stored reference data to calculate the attenuation. In another example, in BUB mode, one transducer is operated as transmitter as well as receiver. The reflected signals are analyzed to check the back-scattered signal attenuation. In the WORM mode, the width of the received maximum is measured from the received signal in transmission mode, when both the transducers are operated as transmitter and receiver respectively. The accuracy of the timing of the various modes and calculations are enhanced using a FPGA that controls the system operations at various modes and calculations.

Thus the bone condition assessment device according to this invention improves the accuracy of the measurement by utilizing four diagnostic parameters obtained by operating the device in different operating modes and by calculating the thickness of the soft tissue surrounding the heel and the amount of squish in the coupling pads. The generation of cross infection among different subjects under diagnosis is prevented by using a disposable gel pad. A removable footpad is used to accommodate feet of different sizes. The use of FPGA controls the operation of different circuit blocks effectively. The structure of device is simplified by using two transducers and operating a single transducer as transceiver in reflection mode.

Thus, various embodiments of this invention provide a bone condition assessment device. Although the invention is described with various specific embodiments, it will be obvious for a person skilled in the art to practice the invention with modifications. However, all such modifications are deemed to be within the scope of the claims.

What is claimed is:

1. An ultrasound based diagnostic device for the analysis of bone conditions in human oscalcis comprising:
   at least two ultrasonic transducers provided at opposite ends of a movable assembly in the main body;
   a set of replaceable and disposable gel pads connected to the transducer assembly;
   a removable foot pad coupled to the transducer assembly;
   a computer processor; and
   a signal processing and acquisition circuit;
   wherein the two ultrasonic transducers are also operated as transmitter and reflector or as transceiver in different operating modes to provide ultrasonic signals to the signal processing and acquisition circuit to calculate four different diagnostic parameters from the received ultrasonic signals from the heel of a subject placed between the transducers against the gel pads, and wherein the device utilizes the diagnostic parameters to calculate thickness of squish of the gel pads and tissue thickness of the heel and the calculated information is provided to the computer processor to determine bone mineral density and bone characteristics of the human.

2. The ultrasound based diagnostic device as set forth in claim 1, wherein-the four measured diagnostic parameters are the speed of sound (SOS), the broadband ultrasonic attenuation (BUA), the broadband ultrasonic back scattering (BUB) and the width of received maximum (WORM) ultrasound signal.

3. The ultrasound based diagnostic device a set forth in claim 1, wherein the two ultrasonic transducers are initially separated by a fixed distance and moved towards each other to accommodate the heel of a subject under diagnosis.

4. The ultrasound based diagnostic device as set forth in claim 1, wherein the transducers emit the ultrasound signals with a frequency range of 10 KHz-1.2 MHz.

5. The ultrasound based diagnostic device as set forth in claim 1, wherein the signal processing and acquisition circuit processes scattered and reflected signals in addition to transmitted signals to calculate parameters to compute the bone mineral density.

6. The ultrasound based diagnostic device as set forth in claim 2, wherein the device is operated in multiple modes so that the BUB, the tissue thickness at the heel coupled with the gel pad squish are measured from the reflected signals, when the transducers are operated as transceivers.

7. The ultrasound based diagnostic device as set forth in claim 2 wherein the BUA and the WORM are acquired from the transmitted signals when two transducers are operated as transmitter and receiver respectively.

8. The ultrasound based diagnostic device as set forth in claim 5, wherein the device utilizes multivariable approach to measure the four diagnostic parameters from the reflected, scattered and transmitted ultrasound signals for improving the accuracy of the diagnosis.

9. The ultrasound based diagnostic device as set forth in claim 2, wherein the device calculates SOS by measuring the tissue thickness at both sides of the heel of the subject instead of assuming a fixed thickness for the tissue surrounding the heel.

10. The ultrasound based diagnostic device as set forth in claim 5, wherein the device measures the squish in the coupling pads on contact with the heel of the-subject from the reflected ultrasound signals.

11. The ultrasound based diagnostic device as set forth in claim 1, wherein the signal processing circuit has a digital signal processor for analyzing the acquired signals from the heel of the subject under diagnosis and a field programmable gate array (FPGA) for controlling the timing and operating modes of device.

12. The ultrasound based diagnostic device as set forth in claim 8, wherein the transducers in the device are operated as transmitter and receiver to calculate bone density at several locations in the human body in addition to the heel.

13. The ultrasound based diagnostic device as set forth in claim 1, wherein the gel pads are easily replaceable, disposable and bacteriostatic to carry out analysis among heels of different subjects under investigation.

14. The ultrasound based diagnostic device as set forth in claim 1, wherein the device has a removable foot pad to position transducers at the desired region of interest in the heel of a subject under analysis.

15. The ultrasound based diagnostic device as set forth in claim 1, wherein the signal processing and acquisition circuit regulates system control, firing, reception and processing operations of ultrasonic signals received from human oscalcis.

16. The ultrasound based diagnostic device as set forth in claim 2, wherein the signal processing and acquisition circuit receives and processes the ultrasonic signals from the heel both in the time and frequency domains to calculate the broadband ultrasonic attenuation and the broadband ultrasonic back scattering.

17. Bone condition evaluating method for estimating osteoporosis using ultrasound based diagnostic device, comprising;
- a) moving at least two transducers provided at opposite ends of a moveable assembly towards each other or away from one another to accommodate a heel of a subject under diagnostic, the heel pressed between two gel pads;
- b) operating the two transducers as transmitter and receiver or as transceiver in different operating modes to transmit and receive ultrasonic signals from the heel of the subject under diagnosis;
- c) activating a signal processing circuit coupled to the transducer assembly to process scattered and reflected ultrasonic signals from the heel in addition to transmitted ultrasonic signals through the heel to calculate parameters including at least tissue thickness of the heel, thickness of squish of the gel pads, speed of sound (SOS), broadband ultrasonic attenuation (BUA) amount, broadband ultrasonic back scattering (BUB) amount and width of the received maximum (WORM) ultrasound signal; and
- d) providing the calculated parameters and the determined tissue thickness of the heel and squish of the gel pads to a computer processor to calculate bone mineral density and bone characteristics.

18. The bone condition evaluating method as set forth in claim 17, wherein the gel pads are replaceable and disposable comprising bacteriostatic material and are connected to the transducer assembly and replaced as needed to prevent cross infection.

19. The bone condition evaluating method as set forth in claim 17, wherein a removable footpad is coupled to the transducer assembly to accommodate various foot sizes and to ensure desired region of interest for analysis.

* * * * *